United States Patent
Lee

(10) Patent No.: US 11,858,989 B2
(45) Date of Patent: Jan. 2, 2024

(54) ANTI-AQP4 ANTIBODIES

(71) Applicant: Chao-Lin Lee, I-Lan (TW)

(72) Inventor: Chao-Lin Lee, I-Lan (TW)

( * ) Notice: Subject to any disclaimer, the term of this patent is extended or adjusted under 35 U.S.C. 154(b) by 130 days.

(21) Appl. No.: 17/131,673

(22) Filed: Dec. 22, 2020

(65) Prior Publication Data

US 2022/0195036 A1    Jun. 23, 2022

(51) Int. Cl.
*C07K 16/28* (2006.01)
*A61K 39/395* (2006.01)
*C07K 14/705* (2006.01)

(52) U.S. Cl.
CPC .......... *C07K 16/28* (2013.01); *C07K 14/705* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| 2015/0139981 A1 | 5/2015 | Verkman et al. |
| 2016/0075748 A1 | 3/2016 | Zamvil et al. |
| 2017/0080063 A1 | 3/2017 | Levy |

OTHER PUBLICATIONS

Rudikoff et al. (1982). PNAS. 79:1979-1983.*

* cited by examiner

*Primary Examiner* — Christine J Saoud
*Assistant Examiner* — Jon M Lockard
(74) *Attorney, Agent, or Firm* — Prosyla Group PC

(57) ABSTRACT

The present disclosure relates to an antibody against Aquaporin-4 (AQP4). These peptide-specific AQP4 antibodies play a role to create a NMO model and contribute for investigating the NMO disease mechanisms and developing the strategy of the treatment.

3 Claims, 10 Drawing Sheets
(7 of 10 Drawing Sheet(s) Filed in Color)

Specification includes a Sequence Listing.

A.

B.

A.

B.

A.

B.

SEQUENCE LISTING

```
<160> NUMBER OF SEQ ID NOS: 2

<210> SEQ ID NO 1
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 1

Thr Pro Pro Ser Val Val Gly Gly Leu Gly Val Thr Thr Val His Gly
1               5                   10                  15

Asn Leu Thr Cys
            20

<210> SEQ ID NO 2
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 2

Cys Ser Met Asn Pro Ala Arg Ser Phe Gly Pro Ala Val Ile Met Gly
1               5                   10                  15

Asn Trp Ala Asn His
            20
```

ANTI-AQP4 ANTIBODIES

The instant application contains a Sequence Listing which has been filed electronically in ASCII format and is hereby incorporated by reference in its entirety. Said ASCII copy, created on Mar. 22, 2021, is named G4590-09800US_Seq-Listing.txt and is 805 bytes in size.

The present disclosure provides an antibody which is produced by the hybridoma cell line AQP002, which has been deposited with the National Institute of Technology and Evaluation (NITE), located in Tokyo, Japan and was given the accession number BP-02882.

FIELD OF THE INVENTION

The present disclosure relates to the field of immunology and medicine. Particularly, the present disclosure relates to an antibody against Aquaporin-4 (AQP4).

BACKGROUND OF THE INVENTION

Neuromyelitis optica (NMO) or Devic's disease is an inflammatory demyelinating disease of the CNS with severe optic neuritis and myelitis. A serum autoantibody has been identified specific for NMO (NMO-IgG), that has been identified as antibody directed against Aquaporin-4 (AQP-4), a high abundant water channel of brain tissue, but as well other tissues.

US 20150139981 relates to a method of treating neuromyelitis optica (NMO) in an animal or human subject comprising administering to the subject a composition comprising an anti-AQP4 antibody deglycosylated at the amino acid position Asn297, thereby treating the NMO in the subject.

US 20160075748 provides human Aquaporin 4 (AQP4) peptides, peptides having homology to human Aquaporin 4 (AQP4) peptides and methods for using human AQP4 peptides and peptides homologous to human AQP4 peptides for diagnosing and/or treating Neuromyelitis Optica.

US 20170080063 provides pharmaceutical compositions for treating neuromyelitis optica (NMO) comprising a therapeutically effective amount of loop C sequence-containing peptide of aquaporin-4 (AQP4) water channel, or a therapeutically effective fragment or variant thereof.

SUMMARY OF THE INVENTION

In one aspect, the present disclosures provide a peptide epitope, comprising a peptide having an amino acid sequence TPPSVVGGLGVTTVHGNLTC (SEQ ID NO: 1) or CSMNPARSFGPAVIMGNWANH (SEQ ID NO: 2).

In one embodiment, the peptide epitope of the present disclosure links to KLH through —SH— bond.

```
mAQP4-Loop:
CKLH-(SH)-TPPSVVGGLGVTTVHGNLTC
(CKLH-(SH_-SEQ ID NO: 1)

mAQP4-Loop:
EKLH-(SH)-CSMNPARSFGPAVIMGNWANH
(EKLH-(SH)-SEQ ID NO: 2)
```

In one aspect, the present disclosures provide an antibody binding to the peptide epitope described herein.

In some embodiments, the antibody is a polyclonal antibody, monoclonal antibody or chimeric antibody or antigen-binding fragments thereof.

In a further embodiment, the antibody is a monoclonal antibody produced by the hybridoma cell line AQP002 deposited at National Institute of Technology and Evaluation (NITE), Tokyo, Japan under the deposit number NITE BP-02882. The antibody specifically binds to the peptide epitope with the sequence of SEQ ID NO:2.

Some embodiments of the invention are directed to modified antibodies that are based on or modified from the mouse anti-AQP4 antibodies exemplified herein. These include, e.g., chimeric, humanized and human anti-AQP4 antibodies.

The invention also provides substantially purified polynucleotides (DNA or RNA) which encode polypeptides comprising segments or domains of the anti-AQP4 antibody chains or antigen-binding molecules described herein.

Also provided in the present disclosures are expression vectors and host cells for producing the anti-AQP4 antibodies described above. Various expression vectors can be employed to express the polynucleotides encoding the anti-AQP4 antibody chains or binding fragments.

The present disclosure further provides pharmaceutical compositions comprising the anti-AQP4 antibodies or antigen-binding molecules formulated together with a pharmaceutically acceptable carrier.

The present disclosure further provides a method for treating and/or preventing NMO, comprising administering an effective amount of an antibody of the invention to a subject.

BRIEF DESCRIPTION OF THE DRAWINGS

The subject patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
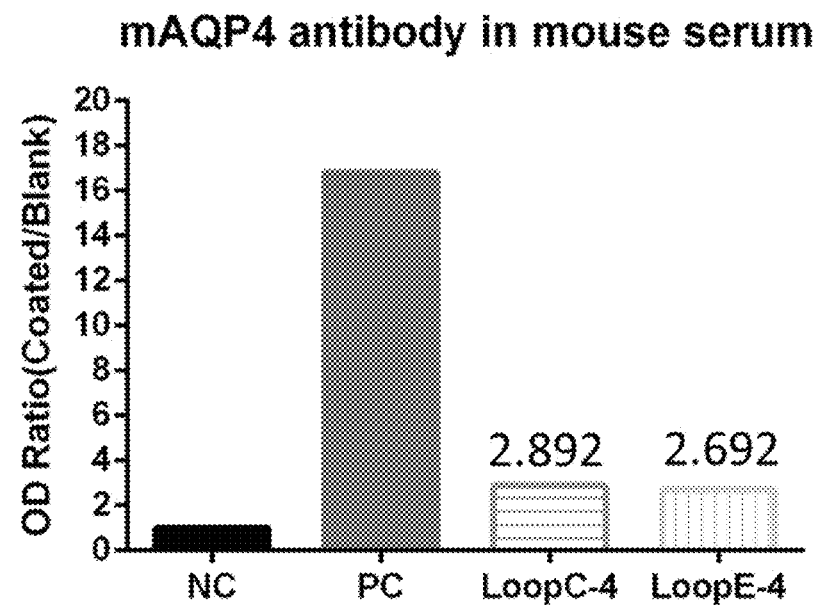
FIG. 1 shows the absorbance of antibodies of the present disclosure in mouse serum. (A) The sera obtained from immunization with LoopC-4 and AQP4-Loop E for 4 days respectively are collected and after EIA assay, it was determined that the sera contain mAQP4 antibodies. (B) The sera obtained from immunization with LoopC-4 and AQP4-Loop E for 7 days respectively are collected and after EIA assay, it was determined that the sera contain mAQP4 antibodies.
Figure 1:
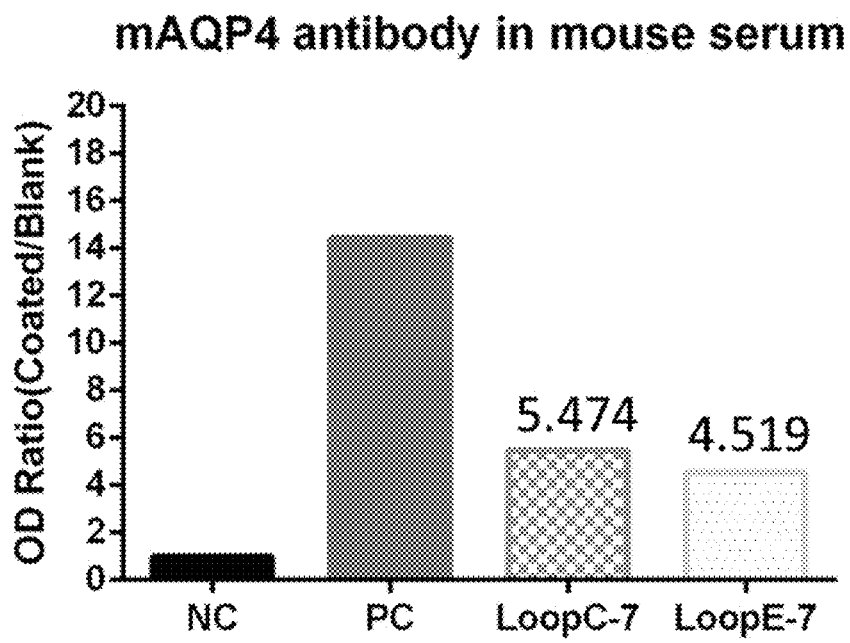

The present disclosures are in part based on the development of monoclonal antibodies that target AQP4.

As may be understood from the earlier discussion, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

The terms "a", "an" and "the" as used herein are defined to mean "one or more" and include the plural unless the context is inappropriate.

As used herein, the term "epitope" refers to any antigenic determinant on an antigen to which the paratope of an antibody binds.

As used herein, the term "amino acid" includes all of the naturally occurring amino acids as well as modified amino acids.

As used herein, the terms "polypeptide", "peptide", and "protein", as used herein, are interchangeable and are defined to mean a biomolecule composed of amino acids linked by a peptide bond.

As used herein, the term "hybridoma" is art recognized and is understood by those of ordinary skill in the art to refer to a cell produced by the fusion of an antibody-producing cell and an immortal cell, e.g. a multiple myeloma cell. Such a hybrid cell is capable of producing a continuous supply of antibody. See the definition of "monoclonal antibody" above and the Examples below for a more detailed description of one art known method of fusion.

As used herein, the term "antibody" is intended to include monoclonal antibodies, polyclonal antibodies, and chimeric antibodies. The antibody may be from recombinant sources and/or produced in transgenic animals. The term "antibody fragment" as used herein is intended to include without limitations Fab, Fab', F(ab').sub.2, scFv, dsFv, ds-scFv, dimers, minibodies, diabodies, and multimers thereof, multispecific antibody fragments and Domain Antibodies. Antibodies can be fragmented using conventional techniques.

As used herein, the term "monoclonal antibody" is also well recognized in the art and refers to an antibody that is mass produced in the laboratory from a single clone and that recognizes only one antigen.

As used herein, the term "therapeutically effective amount" refers to the amount of antibody which, when administered to a human or animal, elicits an immune response which is sufficient to result in a therapeutic effect in said human or animal. The effective amount is readily determined by one of ordinary skill in the art following routine procedures.

The present disclosure uses extracellular domains of AQP4 peptide to induce immune response and establish B cell clone by cell fusion to produce high specificity and affinity AQP4 antibody. The present disclosure successfully selects B cell clone that can produces peptide-specific AQP4 antibodies having high specificity and affinity. These peptide-specific AQP4 antibodies play a role to create a NMO model and contribute for investigating the NMO disease mechanisms and developing the strategy of the treatment.

The present disclosure provides a peptide epitope, comprising a peptide having an amino acid sequence TPPSVVGGLGVTTVHGNLTC (SEQ ID NO: 1) or CSMNPARSFGPAVIMGNWANH (SEQ ID NO:2). The epitope can further links to KLH through —SH— bond. Particularly, the epitope has an amino acid sequence of CKLH-(SH)-TPPSVVGGLGVTTVHGNLTC (CKLH-(SH)-SEQ ID NO: 1; mAQP4-Loop) or EKLH-(SH)-CSMNPARSFGPAVIMGNWANH (EKLH-(SH-SEQ ID NO: 2; mAQP4-Loop).

An immunogenic epitope of a polypeptide is a part of the polypeptide, which elicits an immune response in an animal or a human being, and/or in a biological sample determined by any of the biological assays. A common feature of the polypeptides of the present disclosures is their capability to induce an immunological response as illustrated in the examples. It is understood that a variant of a polypeptide of the invention produced by substitution, insertion, addition or deletion is also immunogenic determined by any of the assays.

The present disclosures provide antibodies or antigen-binding fragments or molecules that specifically bind to AQP4 peptide and extracellular domains thereof. These anti-AQP4 agents are capable of treating and/or preventing NMO disease. Examples of the antibodies include, but are not limited to, polyclonal antibody, monoclonal antibody or chimeric antibody or antigen-binding fragments thereof. In one embodiment, the antibody is an monoclonal antibody produced by the hybridoma cell line AQP002 deposited at National Institute of Technology and Evaluation (NITE), Tokyo, Japan under the deposit number NITE BP-02882. The antibody specifically binds to the peptide epitope with the sequence of SEQ ID NO:2.

Some embodiments of the invention are directed to modified antibodies that are based on or modified from the mouse anti-AQP4 antibodies exemplified herein. These include, e.g., chimeric, humanized and human anti-AQP4 antibodies. Relative to the exemplified antibody, these modified antibodies can have similar binding specificity, as well as improved binding affinity. They also have substantially reduced antigenicity when used in vivo in a non-mouse subject, e.g., a human subject. Some of the modified antibodies are chimeric antibodies which contain partial human immunoglobulin sequences (e.g., constant regions) and partial non-human immunoglobulin sequences. Some other modified antibodies are humanized antibodies. Generally, a humanized antibody has one or more amino acid residues introduced into it from a source that is non-human. The methods can be readily employed to generate humanized anti-AQP4 antibodies of the invention by substituting at least a portion of a CDR from a non-human anti-AQP4 antibody for the corresponding regions of a human antibody. In some embodiments, the humanized anti-AQP4 antibodies of the invention have all three CDRs in each immunoglobulin chain from the exemplified mouse anti-AQP4 antibody grafted into corresponding human framework regions.

Various monoclonal antibodies or antigen-binding fragments with similar binding activities to that of the anti-AQP4 antibodies exemplified herein can be produced. General methods for preparation of monoclonal or polyclonal antibodies are well known in the art. See, e.g., Harlow & Lane, Using Antibodies, A Laboratory Manual, Cold Spring Harbor Laboratory Press, Cold Spring Harbor, N.Y., 1998. The anti-AQP4 antibodies of the present disclosures can be generated by any technique for producing monoclonal antibody well known in the ar. One animal system for preparing hybridomas is the murine system. Hybridoma production in the mouse is a very well-established procedure. After immunization an animal with an appropriate antigen, B cells isolated from the animal are then fused to myeloma cells to generate antibody-producing hybridomas. Monoclonal mouse anti-AQP4 antibodies can be obtained by screening the hybridomas in an ELISA assay using an AQP polypeptide or fusion protein. Immunization protocols and techniques for isolation of immunized splenocytes for fusion are known in the art. Fusion partners (e.g., murine myeloma cells) and fusion procedures are also well known in the art.

Hybridomas secreting anti-AQP4 monoclonal antibodies, or recombinant monoclonal antibodies, can be prepared using methods known in the art. Once a monoclonal antibody specific for the AQP4 protein is identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process and the nucleotide sequences of antibody light and heavy chain genes are determined. For example, many such sequences are disclosed in Kabat, E. A., et al. (1991) Sequences of Proteins of Immunological Interest, Fifth Edition, U.S. Department of Health and Human Services, NIH Publication No. 91-3242. Once obtained, the antibody light and heavy chain sequences are cloned into a recombinant expression vector using standard methods.

The invention provides substantially purified polynucleotides (DNA or RNA) which encode polypeptides comprising segments or domains of the anti-AQP4 antibody chains or antigen-binding molecules described above. Some of the polynucleotides of the invention comprise the nucleotide sequence encoding the heavy chain variable region of exemplified mouse anti-AQP4 antibody. They can alternatively or additionally comprise the nucleotide sequence encoding the light chain variable region of the described anti-AQP4 antibody. Some other polynucleotides of the invention comprise nucleotide sequences that are substantially identical (e.g., at least 80%, 95%, or 99%) to the nucleotide sequence encoding the heavy chain variable region or light chain variable region of an exemplified anti-AQP4 antibody.

Also provided in the present disclosures are expression vectors and host cells for producing the anti-AQP4 antibodies described above. Various expression vectors can be employed to express the polynucleotides encoding the anti-AQP4 antibody chains or binding fragments.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof. Expression vectors of the disclosure can include polynucleotides encoding the antibody or antigen binding porting thereof described herein. In some embodiments, the coding sequences for the antibody or antigen binding porting thereof is operably linked to an expression control sequence. A coding sequence and a gene expression control sequence are said to be operably linked when they are covalently linked in such a way as to place the expression or transcription and/or translation of the coding sequence under the influence or control of the gene expression control sequence.

The anti-AQP4 antibodies described herein can be employed in treating or preventing neuromyelitis optica (NMO). Accordingly, the present disclosures provide a method for treating and/or preventing NMO, comprising administering an effective amount of an antibody of the invention to a subject.

Some embodiments of the invention employ a pharmaceutical composition containing the above-described anti-AQP4 antibody for administration to a subject already affected by a disease or condition caused by or associated with AQP4 (e.g., NMO). The composition contains the antibody or antigen-binding molecules in an amount sufficient to cure, partially arrest, or detectably slow the progression of the condition, and its complications. In prophylactic applications, compositions containing the anti-AQP4 antibodies or antigen-binding molecules are administered to a subject not already suffering from NMO. Rather, they are directed to a subject who is at the risk of, or has a predisposition, to developing such a disorder. Such applications allow the subject to enhance the subject's resistance or to retard the progression of a disorder mediated by AQP4.

The invention provides pharmaceutical compositions comprising the anti-AQP4 antibodies or antigen-binding molecules formulated together with a pharmaceutically acceptable carrier. The compositions can additionally contain other therapeutic agents that are suitable for treating or preventing a given disorder. Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antibody, may be coated in a material to protect the compound from the action of acids and other natural conditions that may inactivate the compound.

The following examples will help describe how the invention is practiced and will illustrate the characteristics of the claimed antibodies and methods.

Examples

Materials and Methods

Animals Used in Study

The wild type C57BL/6J (B6) mice in 6-8 weeks old wee used in animal study. The mice were purchased from National Laboratory Animal Center and hosted according to the regulations of Institutional Animal Care and Use Committee, IACUC.

Cell Line Used in Cell Fusion

NS-1 myeloma cells used in the cell fusion with splenic lymphocyte were cultured in RPMI-1640 medium with 10% FBS. After culturing for several generations, the stabilized cells were freezing stored and used in experiments.

Synthesis of Peptide Epitope

The peptide epitopes, mAQP4-Loop C (mouse AQP4137-155-KLH) and mAQP-Loop E (mouse AQP4211-230-KLH), were synthesized and used to as antigen to induce immune reaction.

Peptide Epitope

```
mAQP4-Loop
CKLH-(SH)-TPPSVVGGLGVTTVHGNLTC
(CKLH-(SH)-SEQ ID NO: 1)

mAQP4-Loop
EKLH-(SH)-CSMNPARSFGPAVIMGNWANH
(EKLH-(SH)-SEQ ID NO: 2)
```

Intrasplenic Immunization

The mice were anesthetized with 30 mg/kg of zoletil 50 and 2% rompun by intraperitoneal injection. The abdominal cavity was open by surgical procedure. 20 μg of peptide epitope mAQP4-Loop C or mAQP4-Loop E was injected to spleen of the mouse. After injection, the abdominal cavity was sutured.

Evaluation of Immune Response

At the 4$^{th}$ day and the 7$^{th}$ day after immunization, blood of the mouse was taken by cardiac puncture. The resulting blood was centrifugated at 3,000 rpm for 10 minutes to collect serum. The serum was subjected to enzyme immunoassay (EIA). Before the EIA was conducted, 100 μL of the antigen (2.5 μg/mL), mAQP4-Loop C or mAQP4-Loop E in coating buffer, was added to each well of the 96-well plate. The solution was discarded and then the plate was washed with washing buffer for three times to remove the antigens unbound to the bottom of the wells. Then, blocking buffer was added to each well and reacted at the room temperature for one hour. After removing the blocking buffer, the plate was washed with washing buffer for three times. The blocking buffer as negative control, AQP4 antibody as positive control and serum with appropriate dilution were added to the wells, respectively, and placed at the room temperature for 2 hours for reaction. The wells were washed by washing buffer 4 times. Then, 50 μL of anti-IgG-HRP was added to each well and reacted for one hour. The wells were washed with washing buffer three times. 50 μL of TMB substrate solution was added each well and reacted 30 minutes under light shade. After color reaction, 50 μL of stop solution was added to each well to quench the reaction. Then, the absorbances were measured at 450 nm by ELISA reader.

Isolation of Spleen Lymphocytes

At the 4$^{th}$ day and the 7$^{th}$ day after immunization, the mice were sacrificed and the spleen was removed from the body. The spleen was mixed with 10 mL of T cell medium and grinded for mixing. The resulting solution was centrifugated at 1,300 rpm for 5 minutes. The supernatant was discarded and then 4 mL of T cell medium was added. After homogenization, 4 mL of cell suspension was slowly added to 3 mL of Ficol-Paque (GE Healthcare, Sweden) and then centrifugated Example 1 Induction of Immune Response Six to eight weeks old of wild type C57BL/6J (B6) female mice were used in intrasplenic injection for immunization. At $4^{th}$ and $7^{th}$ days after immunization, blood was taken from heart of the mice and then centrifugated at 3,000 rpm for 10 minutes to collect serums. The serum samples were subjected to enzyme immunoassay (EIA). The serum samples were added to 96-well plate with or without antigen and then EIA was conducted for the serum samples and the absorbances were detected. The absorbance of the serum sample in the plate with the antigen divides by that without the antigen to obtain OD ratio. The OD ratio greater than 2 represents the presence of antibody in serum sample and the induction of immune response. As shown in FIG. 1, the OD ratios determined at 4t h day after immunization for LoopC-4 and LoopE-4 are 2.892 and 2.692, respectively. The OD ratios determined at 7th day after immunization for LoopC-4 and LoopE-4 are 5.474 and 4.519, respectively.

Example 2 B Cell Lymphocyte Cell Line Secreting Anti-Mouse AQP4 Antibody

Figure 2:
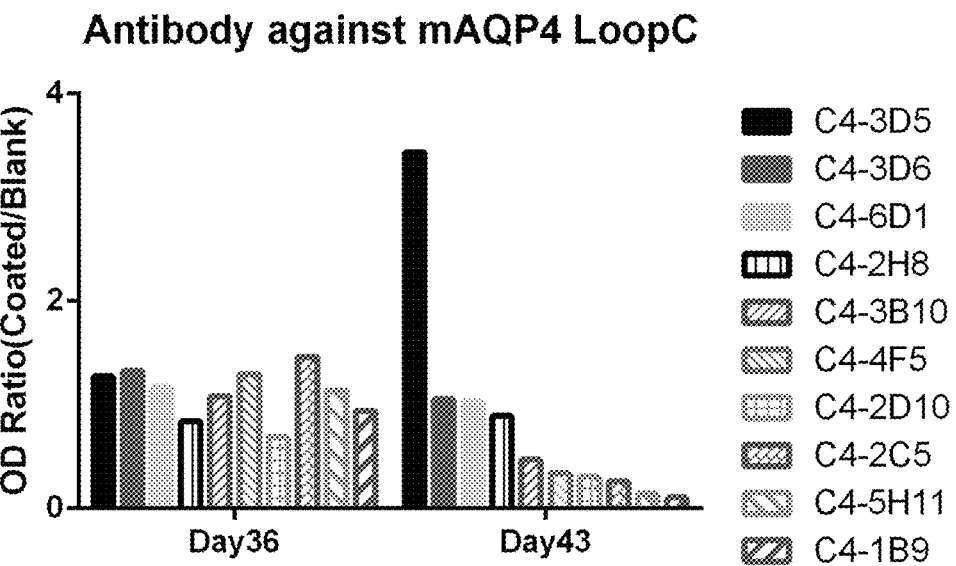
FIG. 2 shows the anti-mouse AQP4 antibodies secreted from B lymphocyte cells after the 4-day immunization in mice. After the third week of cell fusion, the cell supernatant was collected for EIA assay to select B lymphocyte cell lines secreting anti-mouse AQP4 antibodies. (A) After $36^{th}$ say and $43^{rd}$ day of cell fusion, the antibodies in the supernatants of cell hybridomae obtained after 4-day immunization with mAQP4-Loop C were detected. (B) After the $36^{th}$ say and $43^{rd}$ day of cell fusion, the antibodies in the supernatants of cell hybridomae obtained after the 4-day immunization with mAQP4-Loop E were detected. OD ratio ≥2 represents the presence of the antibody. The OD ratio was obtained by dividing the $OD_{absorbance}$ value detected from the binding of the antibody in serum to the coated antigen by the $OD_{absorbance}$ value detected from the control group.
Figure 2:
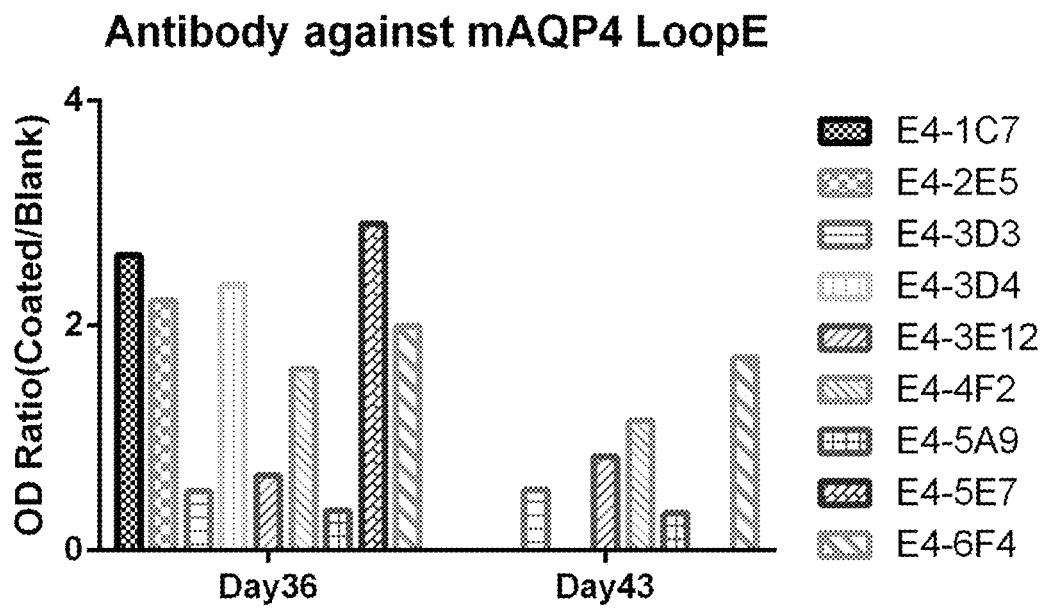
Figure 3:
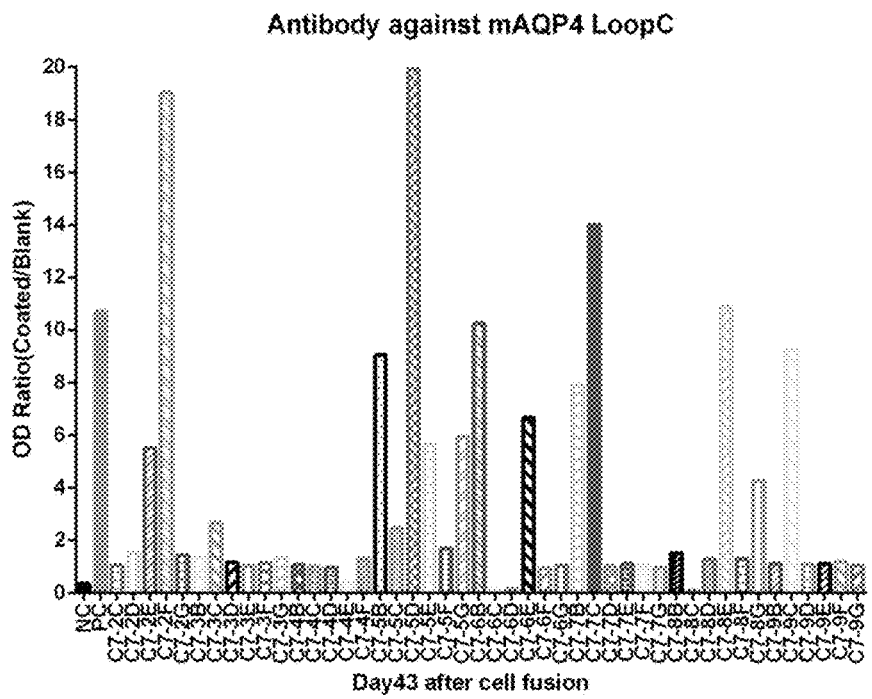
FIG. 3 shows shows the anti-mouse AQP4 antibodies secreted from B lymphocyte cells after 7-day immunization in mice. After the third week of cell fusion, the cell supernatant was collected for EIA assay to select B lymphocyte cell lines secreting anti-mouse AQP4 antibodies. (A) After the $43^{rd}$ day of cell fusion, the antibodies in the supernatants of cell hybridomae obtained after 4-day immunization with mAQP4-Loop E were detected. (B) After the $50^{th}$ day of cell fusion, the antibodies in the supernatants of cell hybridomae obtained after 4-day immunization with mAQP4-Loop E were detected. OD ratio 2 represents the presence of the antibody. The OD ratio was obtained by dividing the $OD_{absorbance}$ value detected from the binding of the antibody in serum to the coated antigen by the $OD_{absorbance}$ value detected from the control group.
Figure 3:
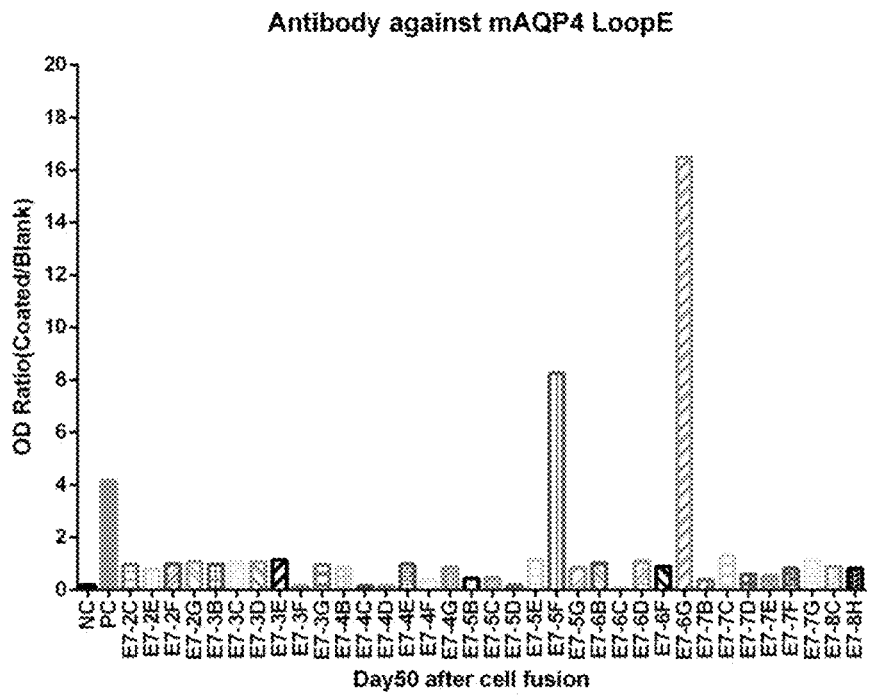

After the immunization with mAQP4-Loop C or mAQP4-Loop E for 4 days or 7 days, the mouse was sacrificed and the spleen was taken out from the mouse. Then, lymphocytes were isolated from the spleen. The resulting lymphocytes were fused with NS-1 myeloma cells and the medium containing 1X HAT was used to select cell hybridoma. The fused hybridoma was cultured in 1X HAT at 37° C., 5% $CO_2$ for 3 weeks. The supernatant was collected and subjected to enzyme immunoassay (EIA) to select B cell lymphocytes secreting anti-mouse AQP4 antibody. The results are shown in FIG. 2 (4-day immunization) and FIG. 3 (7-day immunization).

Figure 4:
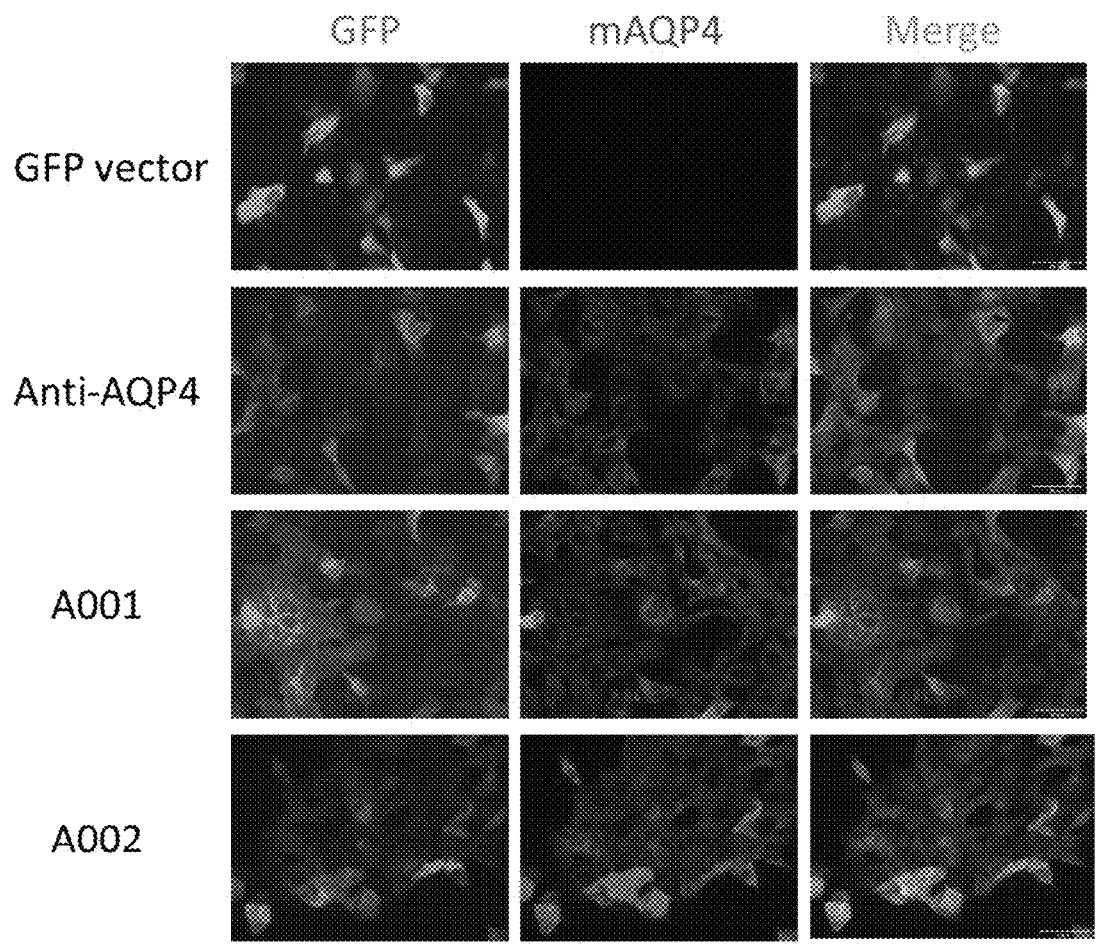
FIG. 4 shows the specificity and affinity of the anti-mouse AQP4 antibody. The B lymphocyte cell lines AQP001 and AQP002 which secreted highest concentrations of anti-mAQP4-Loop C (A001) and anti-mAQP4-Loop E (A002) respectively were selected. The cell culture solution of A001 and A002 were purified using protein G spin column to obtain the anti-mouse AQP4 antibodies. The resulting AQP4 antibodies were conducted IFA assay to obtain specificity and affinity results of the antibodies secreted from the B lymphocyte cell lines after 7-day immunization. The negative control is the anti-AQP4 antibody (Abcam) reacted with eGFP-HEK293 and the positive control is the anti-AQP4 antibody (Abcam) reacted with eGFP-mAQP4-HEK293. The green fluorescence shows the expression of eGFP in the negative control and the expression of the mouse AQP4 protein in the positive control and experimental group (A001 and A002). The red fluorescence shows the expression of the anti-AQP4 antibody in the positive control and the expression of the anti-mAQP4-Loop C antibody and the anti-mAQP4-Loop E antibody in the experimental group.

Four B cell lymphocyte cell lines which secret antibody with highest concentration after immunization of 4 days and 7 days were selected. The anti-mouse AQP4 antibodies were obtained by using protein G spin column and indirect immunofluorescence assay (IFA) to purify the supernatants of cell culture medium. The purified antibodies reacted with HEK293 expressing eGFP-mAQP4. The purified antibody linked to the secondary antibody with fluorescent Cy3 to confirm the specificity and affinity of the antibody to the mouse AQP4. The results show that the anti-mouse AQP4 antibodies (A001 produced from the hybridoma cell line AQP001 and A002 produced from the hybridoma cell line AQP002) produced from the four B cell lymphocyte cell lines have specificity and affinity to the mouse AQP4 protein (see FIG. 4).

Example 2 Competitive Test of Anti-AQP4 Antibody to NMO-IgG

Comparative studies of binding affinity on human AQP4 were conducted in dead cells or living cells using anti-mouse AQP4 antibody and NMO-IgG. For study conducted in dead cells, eGFP-hAQP4-HEK293 cells were fixed using 4% paraformaldehyde and then 1% BSA of blocking buffer was added to the cells. After one hour, 1X PBS was added for washing for 3 times. After washing, A001 and A002 were added to the cells and reacted at 4° C. under dark for 24 hours and then the resulting cells were washed by PB ST for 4 times. Then, NMO-IgG was added to the resulting cells for reaction. After 2 hours, the cells were washed by PB ST for 4 times. Then, anti-human IgG-Cy3 (Jackson ImmunoResearch, 709-165-149) and anti-mouse IgG-DyLight633 (Invitrogen, 35512) were added to the cells, respectively. After reaction for 45 minutes, the resulting cells were washed by PB ST for 3 times and then Fluoromount-G (eBioscienc, USA) was added for mounting. The resulting cells were observed by co-focal microscope (LSM510, Zeiss, Göttingen, Germany).

Figure 5:
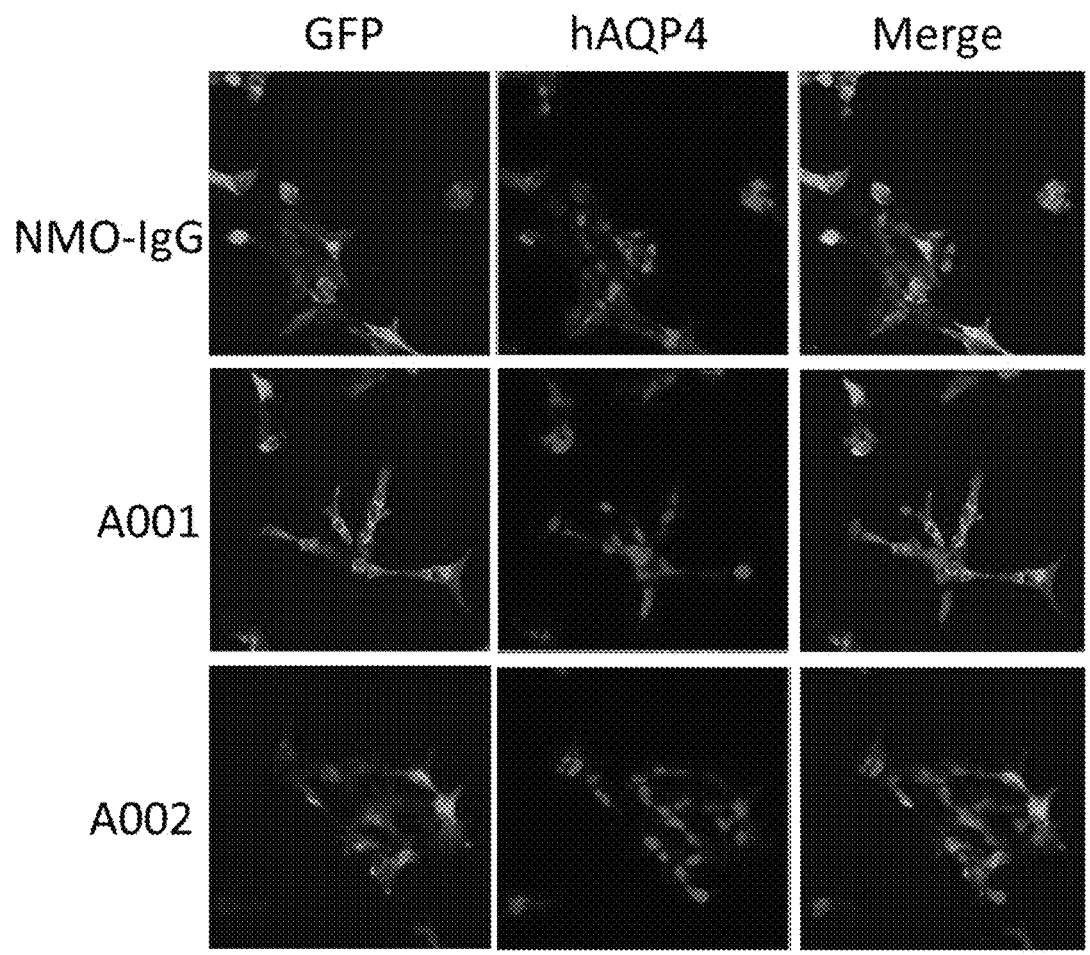
FIG. 5 shows the affinity of the anti-mouse AQP4 antibody binding to the human AQP4. The positive control is the reaction of NMO-IgG with the eGFP-hAQP4-HEK293 (red fluorescence) and the experimental group is the reactions of A001 or A002 with the eGFP-hAQP4-HEK293 (blue fluorescence).
Figure 6:
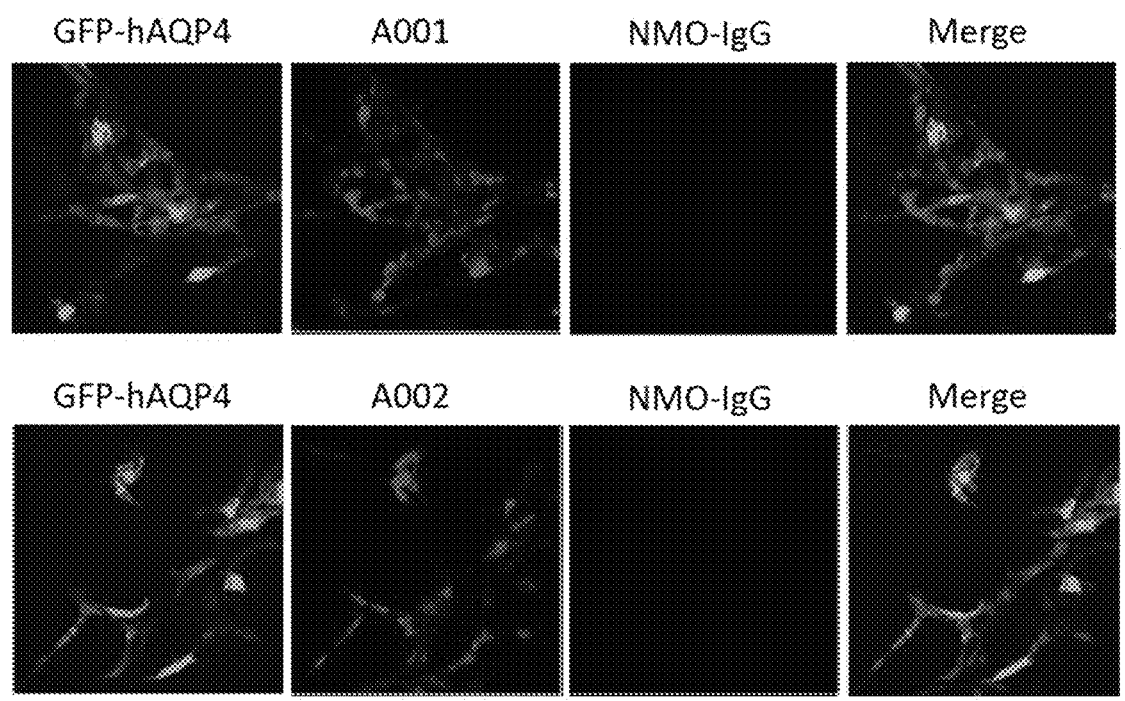
FIG. 6 shows the results of the competitive study of the anti-mouse AQP4 antibody and NMO-IgG. After A001 and A002 were fixed at 4° C. overnight, NMO-IgG was reacted with the fixed A001 and A002 respectively and then dyed with a secondary antibody. The blue florescence shows the reaction of A001 or A002 with the eGFP-hAQP4-HEK293. The red fluorescence shows the reaction of NMO-IgG with the eGFP-hAQP4-HEK293.
Figure 7:
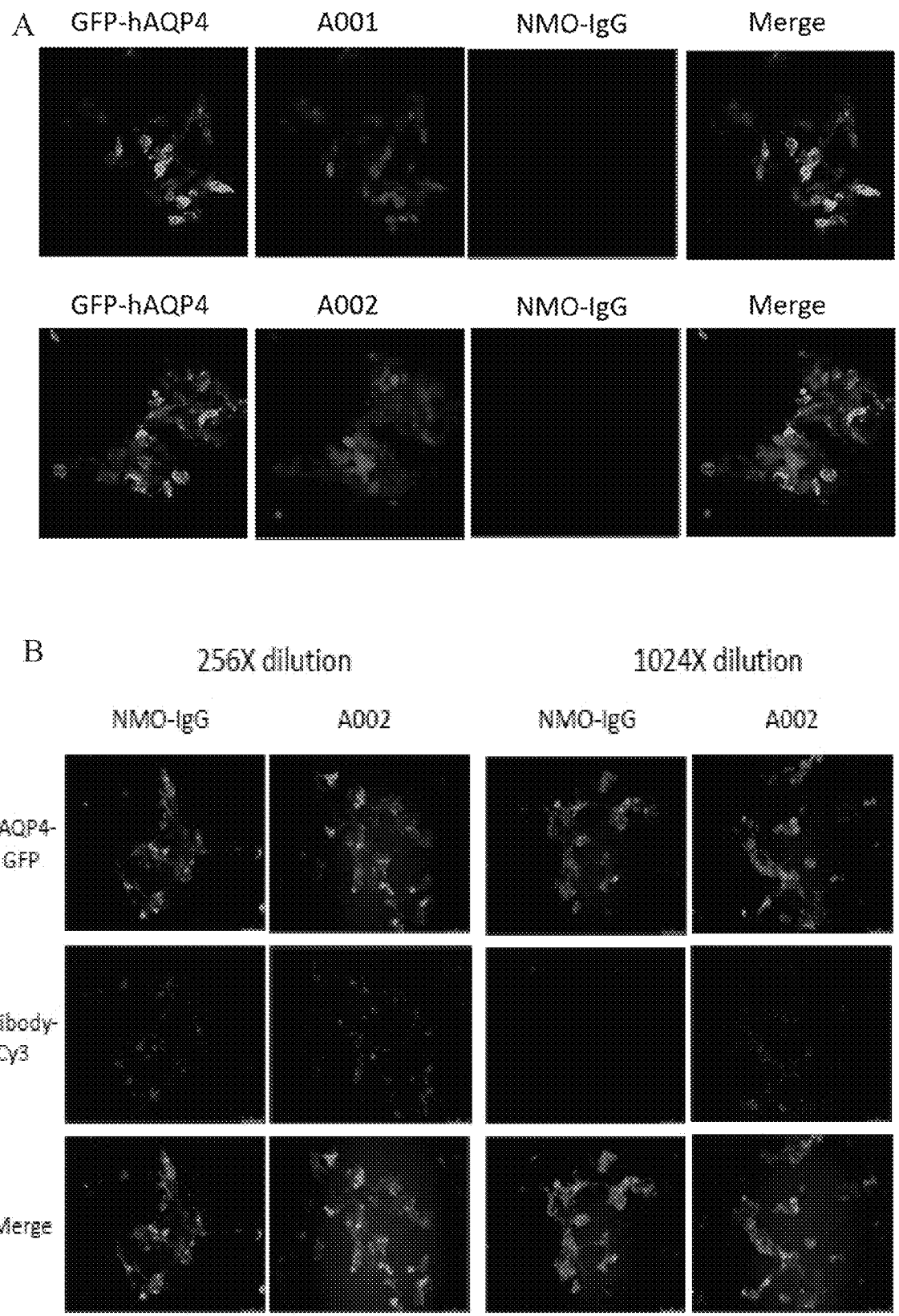
FIGS. 7A, B and C show the results of the competitive study of the anti-mouse AQP4 antibody and NMO-IgG. (A) After A001 and A002 were fixed at 37° C. overnight, NMO-IgG was reacted with the fixed A001 and A002 respectively at 37° C. under 5% $CO_2$ for 24 house and then dyed with a secondary antibody. The blue florescence shows the reaction of A001 or A002 with the eGFP-hAQP4-HEK293 and the red fluorescence shows the reaction of NMO-IgG with the eGFP-hAQP4-HEK293). (B) A002 antibodies compared with NMO-IgG by indirect immunofluorescence. A002 antibodies and NMO-IgG were four-fold serial diluted then indirect immunofluorescence transfected with human AQP4. Green fluorescent (GFP) protein-AQP4 fusion protein. Cy3-labeled donkey anti-human IgG (NMO-IgG) and Cy3-labeled donkey were used as the secondary antibody. Merge was NMO-IgG or A002 antibody binding with HEK293-hAQP4 (orange or yellow). (C) NMO-IgG was incubated in HEK293 transfected with human AQP4 at 37.0 and 5% CO 2 for 2 hours. Then cells treated with A002 Ab or medium at 37.0 and 5% CO 2 for 24 hours. Finally, staining the NMO-IgG or A002 Ab to observe the competition result. Green fluorescent (GFP) protein-AQP4 fusion protein. Cy3-labeled donkey anti-human IgG (NMO-IgG) and DyLight633-labeled goat anti-mouse IgG (A002 antibody) were used as the secondary antibody. Merge was NMO-IgG or A002 antibody binding with HEK293-hAQP4 (C).
Figure 7:
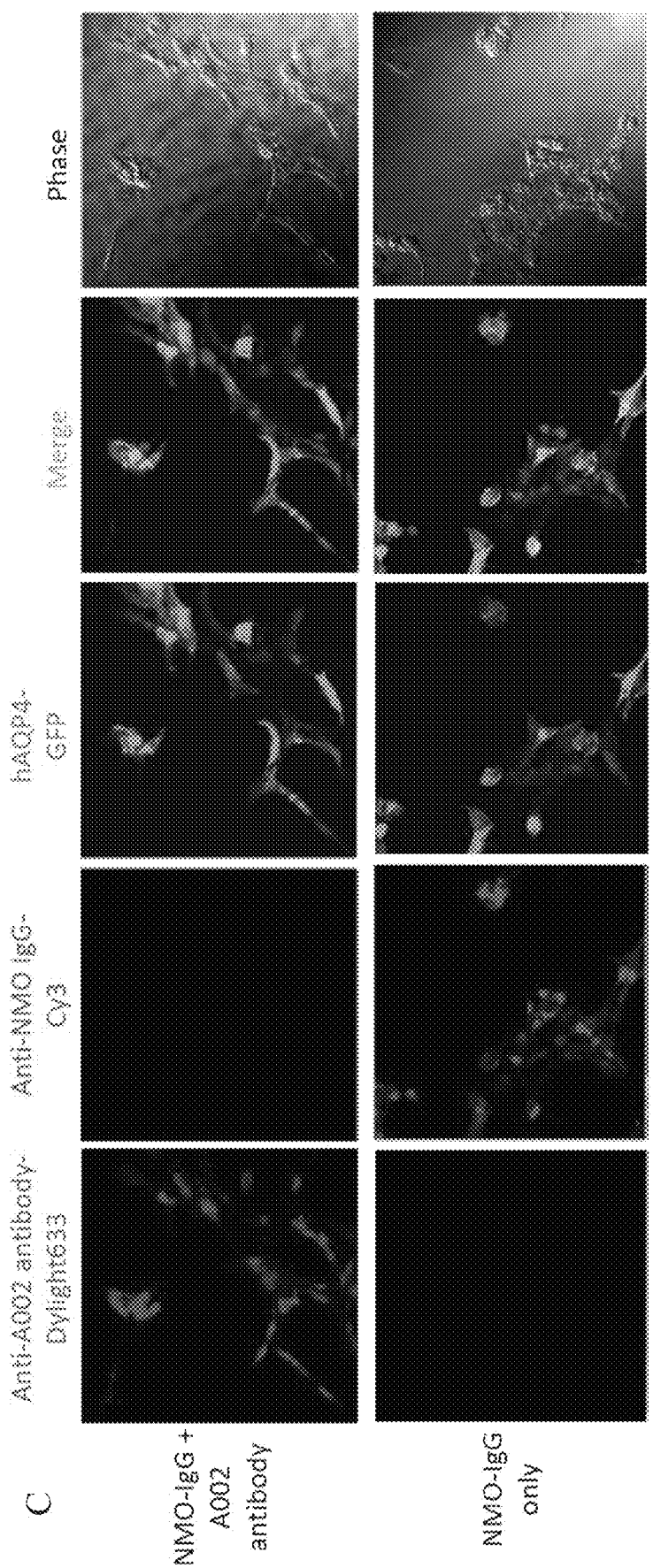

For study conducted in living cells, NMO-IgG was added to eGFP-hAQP4-HEK293 cells. After a reaction at 37° C. under 5% $CO_2$ for 2 hours, A001 and A002 were added to the resulting cells were reacted at 37° C. under 5% $CO_2$ for 24 hours and then washed by 1X PBS for 3 times. After the resulting cells were fixed with 4% paraformaldehyde, permeabilized buffer with 0.1% Triton-X was added to the cells and reacted at room temperature for 10 minutes. Then, blocking buffer with 1% BSA was added to the cells and reacted at room temperature under dark for 1 hour. The resulting cells were washed with 1×PBS for 3 times and then anti-human IgG-Cy3 (Jackson ImmunoResearch, 709-165-149) and nti-mouse IgG-DyLight633 (Invitrogen, 35512) were added to cells and reacted at room temperature under dark for 45 minutes. The resulting cells were washed by PB ST for 3 times. Then, Fluoromount-G (eBioscienc, USA) was added for mounting. The resulting cells were observed by co-focal microscope (LSM510, Zeiss, Gottingen, Germany). The results of the above-mentioned comparative studies were shown in FIGS. 5 to 7.

Example 3 CDC Assay of A002 Monoclonal Ab

Figure 8:
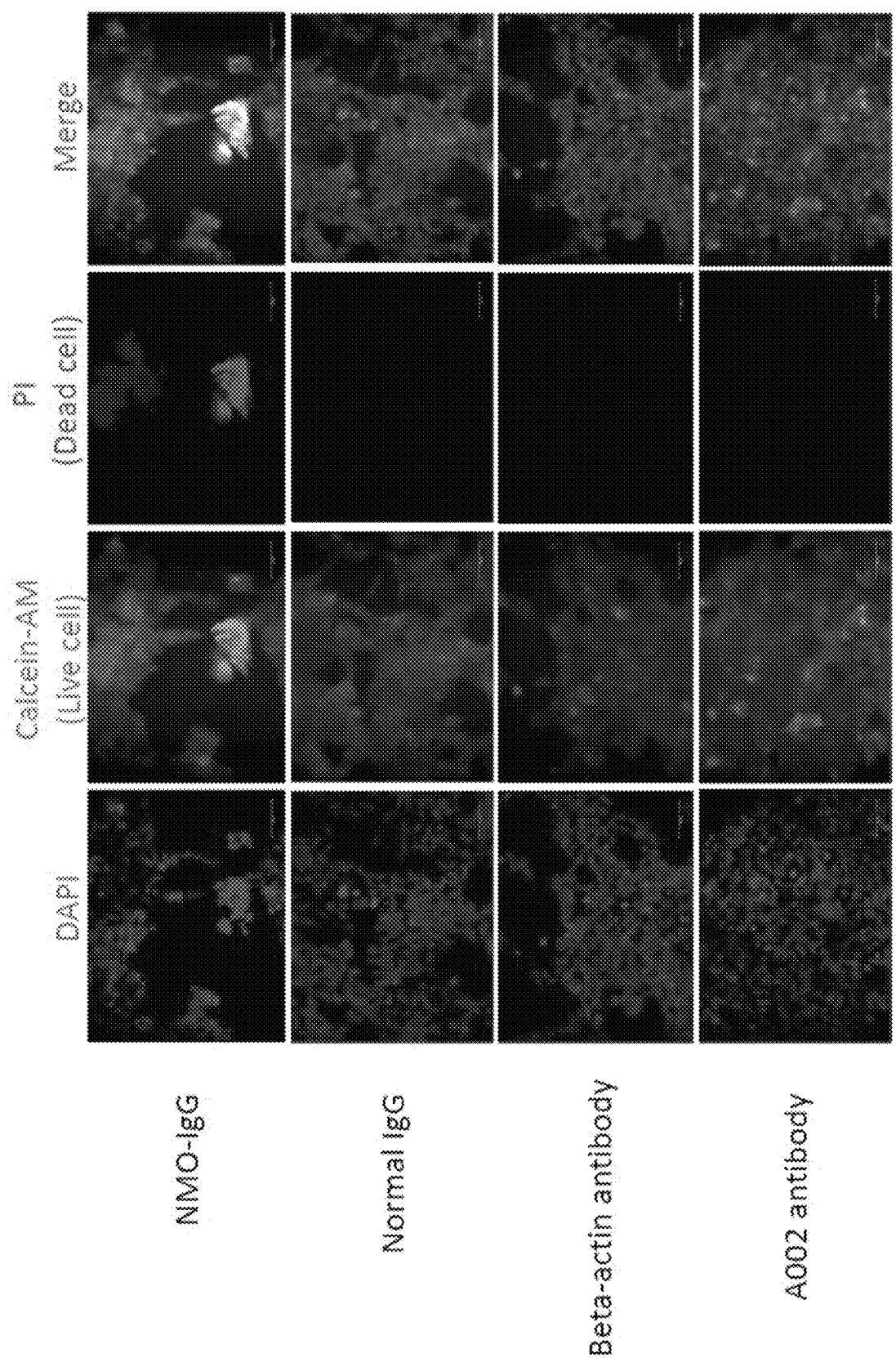
FIG. 8 shows the results of CDC assay of A002 monoclonal Ab. Normal IgG+h-comp: NMO-IgG with human complement; NMO IgG+h-comp: Normal IgG with human complement; A002+h-comp: A002 with human complement; Beta-actin mAb+h-comp: A002 with human complement.

After HEK293 cells were transfected with hAQP4-plasmid DNA for 24 hours, the cells were incubated with NMO-IgG or A002, or with normal human serum (1:20) or anti-beta actin mouse mAb with 5% human complement for 90 min at 37° C. After washed by 1X PBS, cells were incubated with 10 nM Calcein-AM for 15 min at 37° C. Then cells were incubated with 10 μM Propidium Iodide for 15 min at 37° C. after washed. After washed, cells were incubated with 4% formaldehyde for 10 min at room temperature. The images were obtained by microscopy and the results were shown in FIG. 8.

Example 4 Antibody-Dependent Cell-Mediated Cytotoxicity Assay

Figure 9:
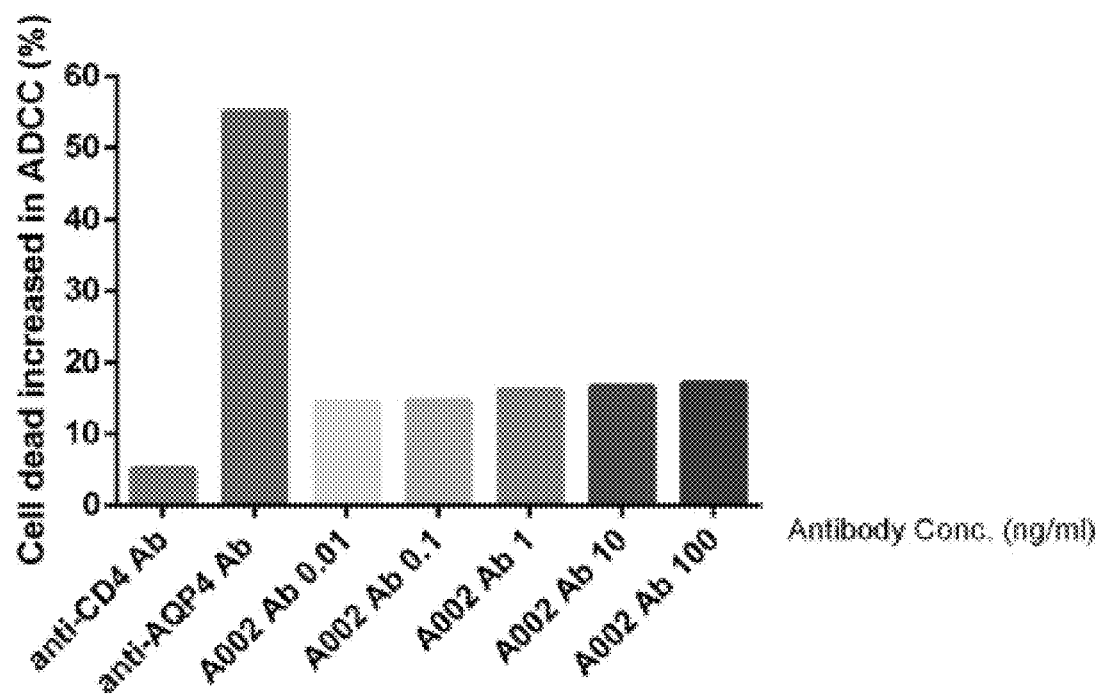
FIG. 9 shows quantification of Propidium Iodide (PI) of cells co-cultured with CD4 antibody, commercial AQP4 antibody or A002 antibody (ten-fold serial dilution).

HEK293-hAQP4-GFP and LPS-stimulated RAW264.7 were co-cultured with CD4 antibody, commercial AQP4 antibody, A002 antibody (ten-fold serial dilution) or culture medium only at 37° C. and 5% CO 2 for 6 hours. Cells were stain with Fixable Far Red-labeled anti-amine, PE-labeled anti-mouse CD11 b then analyzed the % of amine in CD11b-/GFP+ cells. Cell death(%) increased in ADCC=(% cell death in presence of IgG-% cell death in absence of IgG)/(% Cell death in maximum lysis-% cell death in absence of IgG)×100. Antibody-dependent cell-mediated cytotoxicity Assay (ADCC) of A002 antibody by immunofluorescent stain. HEK293-hAQP4-GFP and LPS-stimulated RAW264.7 were co-cultured with CD4 antibody, commercial AQP4 antibody, A002 antibody (ten-fold serial dilution) or culture medium only at 37° C. and 5% $CO_2$ for 6 hours. Then cells were stain with Propidium Iodide (PI). Histograms show quantification of Propidium Iodide (PI) of cells co-cultured with CD4 antibody, commercial AQP4 antibody or A002 antibody (ten-fold serial dilution) (FIG. 9). PI intensity was adjusted by Subtracting PI intensity of cells co-cultured with culture medium only.

Example 5 Mouse Ig Isotyping Assay

Figure 10:
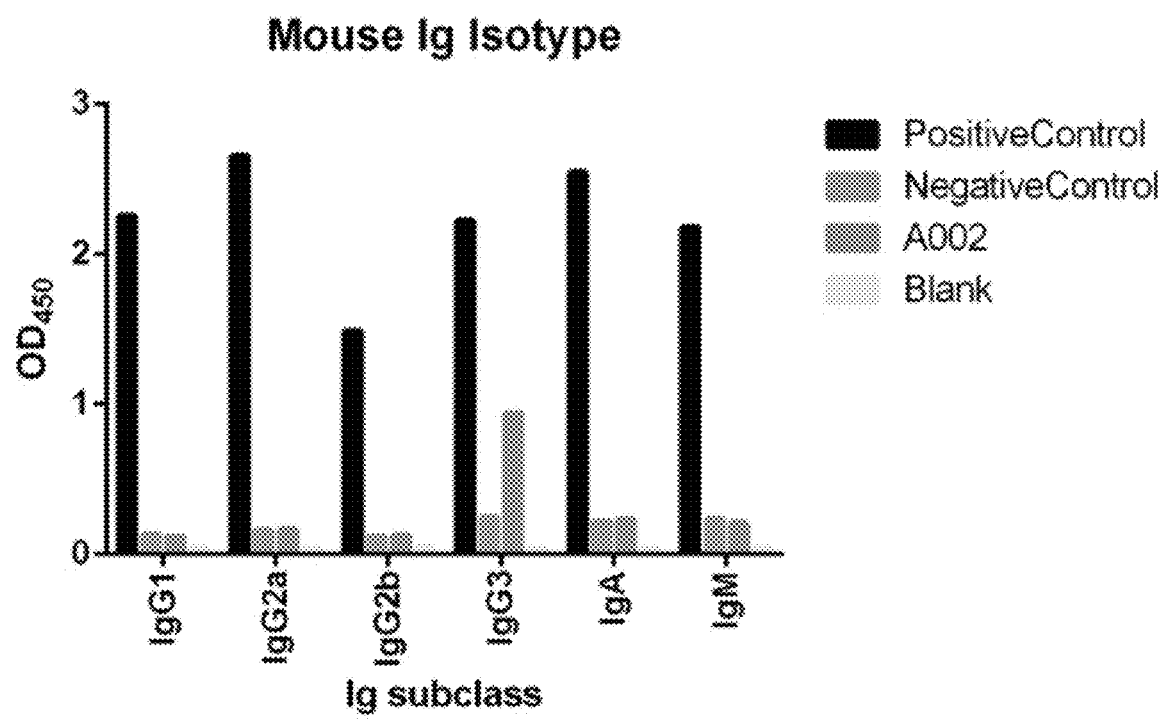
FIG. 10 shows mouse Ig Isotyping of A002 antibody.

Mouse Ig Isotyping of A002 antibody. A002 Ab was diluted to 100 ng/μl as working concentration and analyzed by Mouse Ig Isotyping Instant ELISA Kit (Invitrogen). After reading absorbance of 450 nm by ELISA reader (BioTek, USA), A002 antibody was classified to mouse IgG subtype, IgG3 (FIG. 10).

We claim:

1. An antibody produced by the hybridoma cell line AQP002 deposited at National Institute of Technology and Evaluation (NITE), Tokyo, Japan under the deposit number NITE BP-02882, or antigen-binding molecule thereof, wherein the antibody or antigen-binding fragment thereof binds to a peptide epitope having the amino acid sequence of SEQ ID NO:1 or SEQ ID NO:2.

2. A composition comprising the antibody or antigen-binding fragment thereof of claim 1, and a pharmaceutically acceptable vehicle.

3. A hybridoma cell line AQP002 deposited at National Institute of Technology and Evaluation (NITE), Tokyo, Japan under the deposit number NITE BP-02882.

* * * * *